US012622593B2

(12) United States Patent
Bahmanyar et al.

(10) Patent No.: US 12,622,593 B2
(45) Date of Patent: May 12, 2026

(54) PRESSURE SENSOR

(71) Applicant: IMPERIAL COLLEGE INNOVATIONS LIMITED, London (GB)

(72) Inventors: Mohammad Reza Bahmanyar, London (GB); Longfang Zou, London (GB)

(73) Assignee: IMPERIAL COLLEGE INNOVATIONS LIMITED, London (GB)

( * ) Notice: Subject to any disclaimer, the term of this patent is extended or adjusted under 35 U.S.C. 154(b) by 844 days.

(21) Appl. No.: 17/909,915

(22) PCT Filed: Mar. 9, 2021

(86) PCT No.: PCT/GB2021/050583
§ 371 (c)(1),
(2) Date: Sep. 7, 2022

(87) PCT Pub. No.: WO2021/181083
PCT Pub. Date: Sep. 16, 2021

(65) Prior Publication Data
US 2023/0106499 A1     Apr. 6, 2023

(30) Foreign Application Priority Data

Mar. 9, 2020     (GB) ...................................... 2003380

(51) Int. Cl.
*A61B 5/03*          (2006.01)
*A61B 5/00*          (2006.01)
(Continued)

(52) U.S. Cl.
CPC ............ *A61B 5/031* (2013.01); *A61B 5/6868* (2013.01); *G01L 9/0016* (2013.01);
(Continued)

(58) Field of Classification Search
None
See application file for complete search history.

(56) References Cited

U.S. PATENT DOCUMENTS

| | | | | | |
|---|---|---|---|---|---|
| 3,811,427 | A | * | 5/1974 | Kresse | G01L 9/0052 |
| | | | | | 600/488 |
| 4,006,628 | A | * | 2/1977 | St. Jacques | G01L 9/0085 |
| | | | | | 336/134 |

(Continued)

FOREIGN PATENT DOCUMENTS

| | | |
|---|---|---|
| EP | 1837638 A1 | 9/2007 |
| GB | 2571141 A | 8/2019 |

(Continued)

OTHER PUBLICATIONS

UKIPO Search Report for GB2003380.9 dated Sep. 10, 2020.
(Continued)

*Primary Examiner* — Jacqueline Cheng
*Assistant Examiner* — Samuel C Kim
(74) *Attorney, Agent, or Firm* — Fennemore Craig, P.C.

(57)     ABSTRACT

A pressure sensing apparatus comprises an elongate first sensor device in a beam configuration supported at at least one longitudinal end by a rigid support structure and having a deflectable portion. A chamber is disposed adjacent a first, internally-facing, face of the first sensor device. An envelope hermetically seals the first sensor device and the chamber from an ambient environment external to the pressure sensing apparatus. The envelope comprises a flexible membrane disposed over and coupled to a second, externally-facing, face of the first sensor device and extending along at least one or two sides of the first sensor device and the chamber. The sensor device may be a surface acoustic wave device coupled to an RF antenna.

20 Claims, 11 Drawing Sheets

(51) Int. Cl.
*G01L 9/00* (2006.01)
*G01L 19/14* (2006.01)
*A61M 27/00* (2006.01)

(52) U.S. Cl.
CPC .......... *G01L 9/0025* (2013.01); *G01L 19/149* (2013.01); *A61B 2562/0247* (2013.01); *A61M 27/006* (2013.01)

(56) References Cited

U.S. PATENT DOCUMENTS

| | | | |
|---|---|---|---|
| 6,432,050 | B1 | 8/2002 | Porat et al. |
| 6,571,638 | B2 * | 6/2003 | Hines ................. G01L 19/0092 73/702 |
| 7,100,451 | B2 * | 9/2006 | Solie ..................... G01L 9/0025 73/703 |
| 7,146,861 | B1 | 12/2006 | Cook et al. |
| 2004/0111022 | A1 * | 6/2004 | Grabek ............... G01R 33/285 600/423 |
| 2005/0225214 | A1 * | 10/2005 | Kalinin .............. G01L 19/0092 310/348 |
| 2007/0089525 | A1 * | 4/2007 | Momose .............. G01L 9/0025 73/753 |
| 2010/0010328 | A1 * | 1/2010 | Nguyen .............. A61B 5/0215 600/364 |
| 2010/0217108 | A1 | 8/2010 | Tauber et al. |
| 2012/0265028 | A1 | 10/2012 | Hughes et al. |
| 2013/0226066 | A1 * | 8/2013 | Liu ..................... A61M 27/006 604/9 |
| 2018/0372563 | A1 * | 12/2018 | Rogers ................ H01Q 9/0428 |
| 2019/0290207 | A1 * | 9/2019 | Wright ................ A61B 5/6851 |

FOREIGN PATENT DOCUMENTS

| | | | |
|---|---|---|---|
| GB | 2571142 | A | 8/2019 |
| WO | 2012112819 | A2 | 8/2012 |
| WO | 2015161102 | A1 | 10/2015 |
| WO | 2017013655 | A1 | 1/2017 |
| WO | 2018055367 | A2 | 3/2018 |
| WO | 2019162672 | A1 | 8/2019 |

OTHER PUBLICATIONS

International Search Report and Written Opinion for PCT/GB2021/050583 dated Jun. 4, 2021.
International Preliminary Report on Patentability for PCT/GB2021/050583 dated Sep. 9, 2022.
A surface acoustic wave ICP sensor with good temperature stability by Bing Zhanga , Hong Hua; , Aipeng Yeb and Peng Zhanga Department of Mechanical Engineering and Automation, Harbin Institute of Technology Shenzhen Graduate School, Shenzhen, Guangdong, China College of Mechatronics and Control Engineering, Shenzhen University, Shenzhen, Guangdong, China— Technology and Health Care, vol. 25, No. S1, pp. 435-441, (2017).
UKIPO Search Report for GB2003380.9 dated Jul. 3, 2023.

* cited by examiner

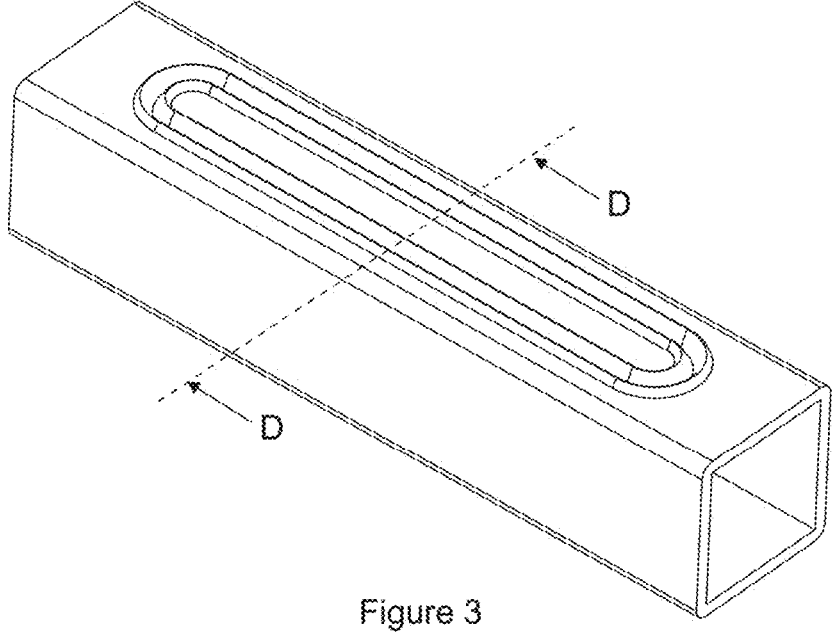
Figure 3
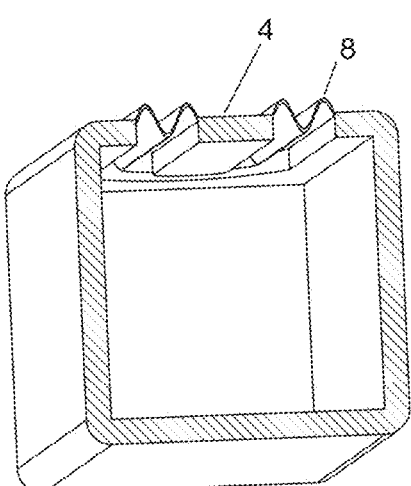
Cross-Section along D-D

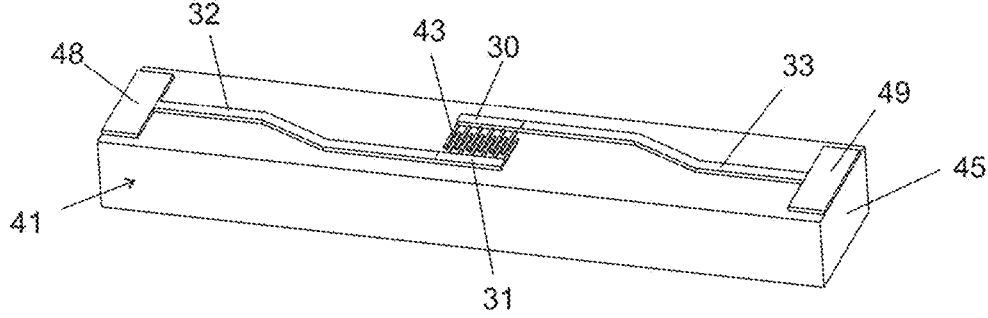
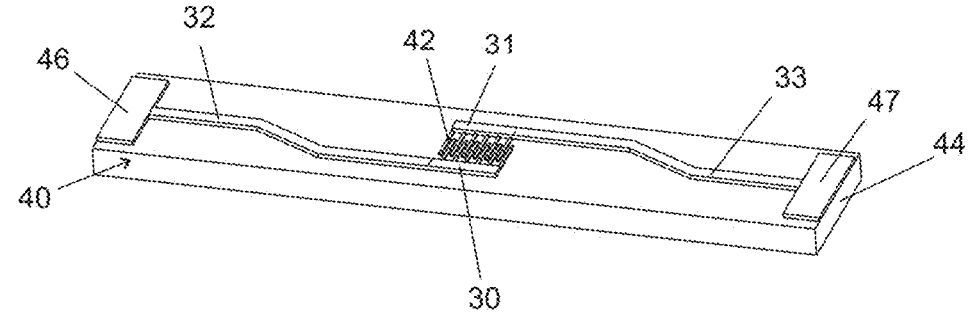
Figure 4
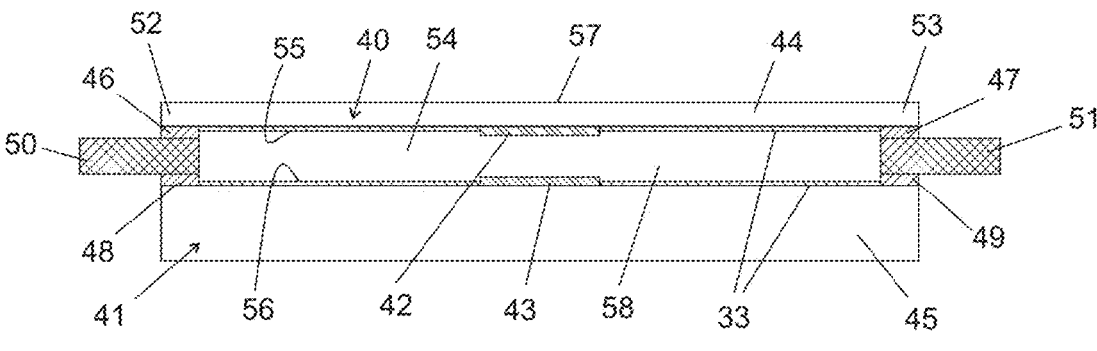
Figure 5

Surface: Total displacement (mm)

Surface: Von Mises Stress (N/m²)

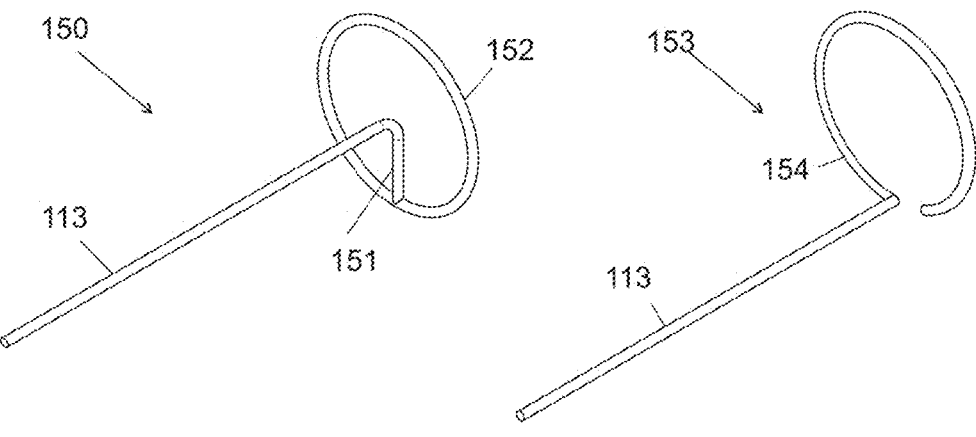
Figure 15a                    Figure 15b
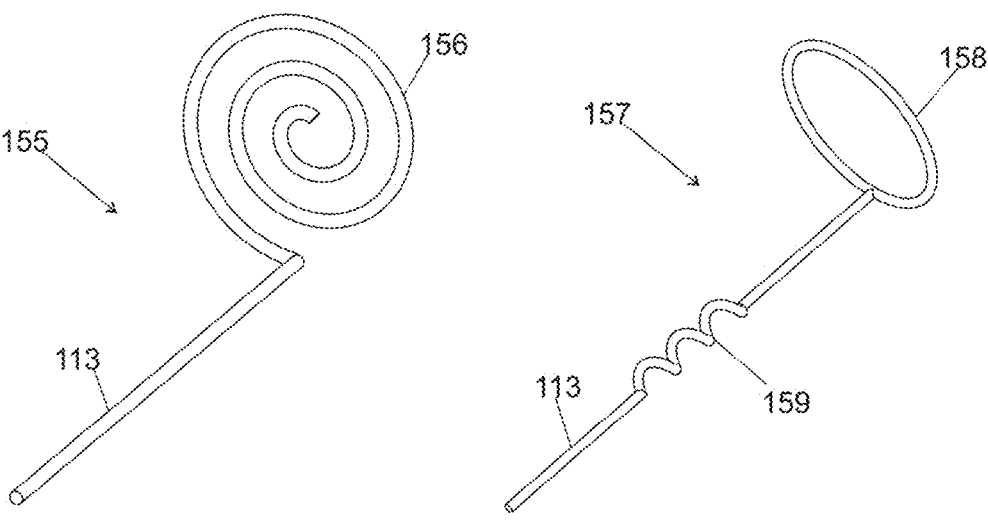
Figure 15c                    Figure 15d

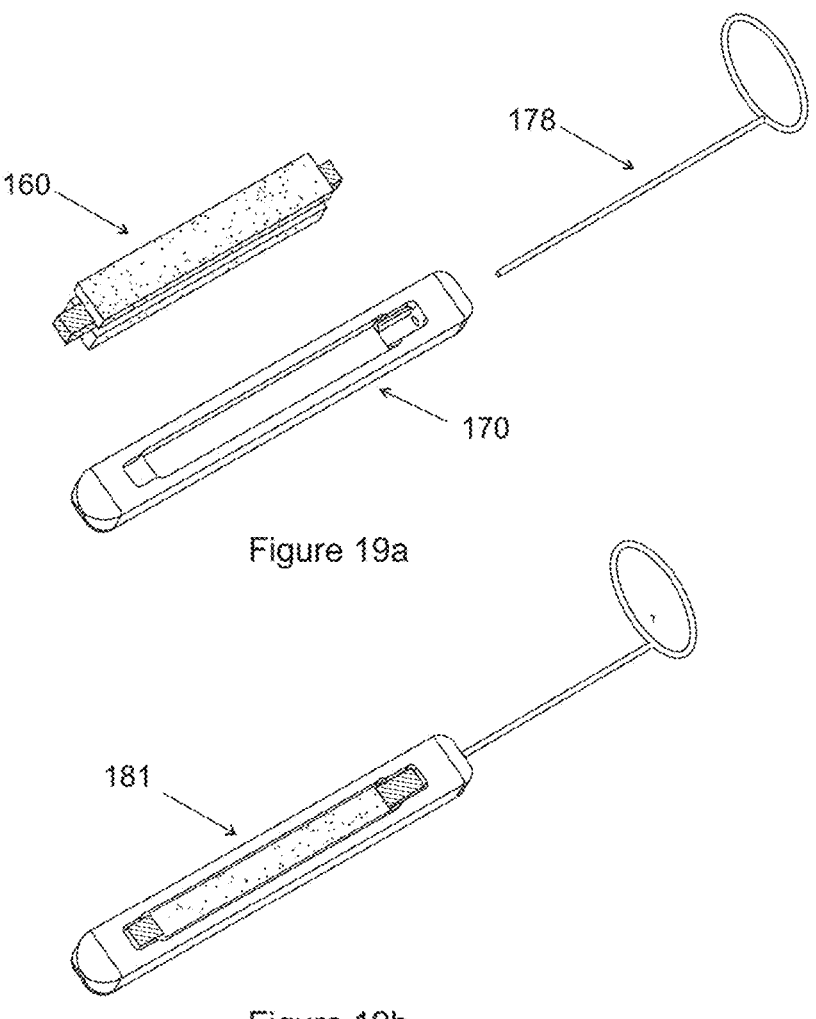
Figure 19a
Figure 19b
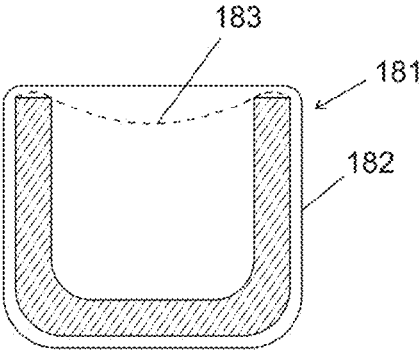
Figure 20

PRESSURE SENSOR

The present disclosure relates to pressure sensors operable to monitor an ambient pressure by deflection of an element within an enclosure by pressure exerted on the enclosure via a flexible membrane.

Elevated intracranial pressure (ICP) is a dangerous condition that can be caused by severe head injuries and other pathological problems. Continuous and accurate measurement of intracranial pressure (ICP) is considered a valuable means of management of patients suffering from ICP hypertension. The volume of the intracranial cavity is constant under normal conditions. The maintenance of a steady ICP depends on the volume of its contents, which include brain tissue (~80%), venous blood (~3 to 4%), arterial blood (~6 to 7%) and cerebrospinal fluid (CSF) (~10%). As brain tissue is relatively incompressible, steady ICP requires balancing the inflow and outflow of the fluid components. In other words, there must be a balance between the inflow of arterial blood and the outflow of venous blood from the head, as well as between the rate of CSF production and drainage. Some changes in mean ICP are expected under regular physiologic conditions, including changes in posture, brain activity, cardiovascular function, respiratory function and adrenergic tone.

Elevated ICP can result from any mechanism that increases the volume of blood or CSF. Alternatively, ICP can also increase by the addition of a fourth component, such as a mass, intracranial haemorrhage or cerebral oedema that expands beyond the ability of the system to compensate. As ICP increases, mean arterial pressure (MAP) is increased, primarily through a rise in cardiac output, in order to maintain a steady cerebral perfusion pressure (CPP), which represents the pressure gradient driving cerebral blood flow and hence oxygen and metabolite delivery. In the presence of elevated ICP beyond the ability for compensation through elevation of MAP, CPP will be compromised and cerebral ischemia may follow. When ICP is sufficiently elevated, the pressure differential between the intracranial cavity and the spinal canal can cause the downward motion of brain tissue (i.e., herniation), which can compress vital brainstem structures, and subsequently lead to severe neurological outcomes including death. Untreated hydrocephalus has a 50-60% death rate, while survivors having varying degrees of intellectual, physical, and neurological disabilities.

The most common neurological and neurosurgical pathologies that require ICP monitoring are traumatic brain injury (TBI), subarachnoid hemorrhage (SAH), and hydrocephalus.

Conventional invasive ICP monitoring systems require a wire, optical fibre or tube penetration of the skin. Such wired systems may limit patient transport and movement and may have high risks of infection, which can prevent long term usage. Some commercial telemetry ICP systems may offer the possibility of long term and continuous ICP monitoring. However, the sizes of the implantable and external device components and the cost of the system can limit their applications due to the wireless transmission method of inductive coupling, which, in nature, requires large coils.

Elevated ICP can be treated by intracranial shunts, i.e. tubes that drain CSF into other parts of body (e.g. the abdomen). Shunts may be made from two tubes. One is inserted into the ventricle at one end and connected to a valve at the other end. The valve adjusts CSF flow from the brain into the second tube. However, current technology shunts can be prone to failures because of issues ranging from shunt obstruction, disconnections, fracture, over drainage or underdrainage. Therefore a 'smart shunt', i.e. a shunt integrated with a wirelessly readable pressure sensor, is desirable to improve reliability, control, precision and monitoring.

It is desirable to provide a pressure sensor that can have some or all of the following features: to be fabricated to have a very small size; to be wirelessly readable; to be powered using wireless technology.

As reproduced in FIGS. 1 to 3 of this disclosure, GB 2571141 describes an implantable cardiovascular pressure sensor 1 which comprises rigid enclosure 2 arranged for holding a compressible fluid or a vacuum 3 sealed within the rigid enclosure by a flexible membrane 4. An elongate compliant member 5 comprising a piezoelectric material is provided within the enclosure and the flexible membrane 4 is coupled to the elongate compliant member 5 to transfer external fluid pressure load 6 to the elongate compliant member 5 to cause deflection of the elongate compliant member 5. The pressure sensor 1 comprises a first acoustic wave device 10 provided by the piezoelectric material of the elongate compliant member 5 for sensing deflection of the elongate compliant member 5.

The membrane 4 may include at least one flexible feature arranged to reduce rigidity in the membrane. For example, such a flexible feature may include a corrugation of the membrane 4 arranged to reduce strain placed on the membrane by deformation. As seen in FIGS. 1 and 2 the corrugation may comprise a ridge 7 towards the ends/sides of the membrane 4. The ridge 7 may extend around the perimeter of the membrane 4 to provide a flexible connection between the compliant member 5 and the rigid enclosure 2. As seen in FIG. 3, the corrugation may comprise ridges 8 (such as folds or bends) in the surface of the membrane 4. These may follow a closed path (which may be curved in places) that circumscribe the elongate compliant member 5 about the surface of the sensor.

It is an object of the invention to provide improvements in pressure sensors such as that described in GB 2571141 as discussed above.

According to one aspect, the invention provides a pressure sensing apparatus comprising:

an elongate first sensor device in a beam configuration supported at at least one longitudinal end by a rigid support structure and having a deflectable portion;

a chamber disposed adjacent a first, internally-facing, face of the first sensor device;

an envelope hermetically sealing the first sensor device and chamber from an ambient environment;

the envelope comprising a flexible membrane disposed over and coupled to a second, externally-facing, face of the first sensor device and extending along at least one or two sides of the first sensor device and the chamber.

The pressure sensing apparatus may be configured such that inward pressure applied to the flexible membrane at the second face causes inward deflection of the flexible membrane disposed over the deflectable portion of the first sensor device and inward and/or outward displacement of the flexible membrane along said at least one or two sides of the first sensor device and the chamber. The flexible membrane of the envelope may surround the first sensor device, the chamber and the support structure along at least a portion of the longitudinal axis of the first sensor device. The flexible membrane may form a sleeve extending along the longitudinal axis and around the first sensor device, the chamber and at least a portion of the support structure. The support structure may comprise two longitudinal end portions which each close a respective end of the sleeve to form the hermetic seal of the envelope. The elongate first sensor device may be supported at each longitudinal end by the rigid support structure and the deflectable portion may be a deflectable central portion between the opposing longitudinal ends. A base of the rigid support structure may comprise a second sensor device extending parallel to the first sensor device adjacent the chamber. The rigid support structure may further comprise a pair of spacers separating the base and first sensor to form the chamber. The spacers may each comprise an electrically conductive material coupled to a respective electrical terminal of at least one of the first sensor device and the second sensor device. The envelope may comprise an electrically conductive material electrically coupled to a first one of the spacers which may form a ground plane enveloping at least a substantial part of the first sensor device. The longitudinal end portions may each comprise an electrically conductive cap. Each cap may be bonded to a respective end of the sleeve around its circumference to form the hermetic seal.

The electrically conductive material of a second one of the spacers may be electrically connected to an antenna extending away from the envelope. The antenna may comprise a resilient material having an expanded shape memory configuration. The antenna may define a substantially linear axial portion and an off-axis laterally extending portion. The material may be resiliently bendable into a substantially linear configuration for delivery of the apparatus via a catheter.

The flexible membrane may comprise a metal material soldered, welded or otherwise bonded directly to at least one electrically conductive end cap of the envelope. The flexible membrane may comprise a metallised polymer bonded to at least one electrically conductive end cap of the envelope and electrically continuous therewith by an electroplated layer. The flexible membrane may comprise a glass material forming the envelope as a closed-ended capsule sealed around at least one electrical connection passing therethrough. The closed-ended capsule may be sealed around at least two electrical connections passing therethrough, and may further include an electrically conductive sleeve disposed around the capsule electrically connected to one of the electrical connections to form a ground plane around the capsule.

The rigid support structure may comprise a housing having a trench within which the first sensor device is positioned, and the flexible membrane may comprise a polymer which encapsulates the housing to form the envelope. The housing may comprise first and second electrically conductive portions separated from one another by an electrically insulating portion, and each electrically conductive portion may be coupled to a respective electrical terminal of the first sensor device. The first electrically conductive portion of the housing may be substantially longer than the second electrically conductive portion to form a ground plane, and the second electrically conductive portion of the housing may be coupled to an antenna. The trench of the housing may be narrower at the ends to support the respective electrical terminals of the first sensor device and may be wider therebetween to enable unrestricted displacement of the deflectable portion at one or two sides of the first sensor device. The flexible membrane may be coated with one or more layers of material to increase the hermeticity of the envelope.

The pressure sensing apparatus may be incorporated within an intracranial shunt apparatus. The pressure sensing apparatus may further include a valve within the intracranial shunt apparatus. The valve may be configured for control by an output of at least the elongate first sensor device.

Embodiments of the present invention will now be described by way of example and with reference to the accompanying drawings in which:

FIG. 3 is a schematic perspective view of a part of a prior art pressure sensor as discussed above, and a cross-sectional end view on line D-D;

FIG. 4 is a schematic perspective view of pressure sensing devices for use in a pressure sensing apparatus;

FIG. 5 is a schematic cross-sectional side view of the pressure sensing devices of FIG. 4 in a partially assembled pressure sensing apparatus;

FIG. 8 is a 3D simulation of surface displacement in the enclosure of FIG. 6a;

FIGS. 15a to 15d are schematic perspective views of various antenna configurations;

FIGS. 19a and 19b are schematic perspective views showing assembly of the pressure sensing apparatus of FIG. 16 within the housing of FIG. 18; and FIG. 20 is a schematic cross-sectional end view of the housing of FIG. 19b after encapsulation.

Figure 1:
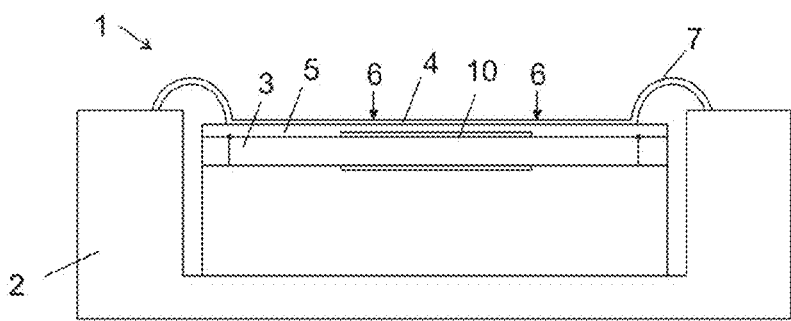
FIG. 1 is a schematic cross-sectional side view of a prior art pressure sensor as discussed above.

Throughout the present specification, descriptors relating to relative orientation and position, such as "top", "bottom", "horizontal", "vertical", "left", "right", "up", "down", "front", "back", as well as any adjective and adverb derivatives thereof, are used in the sense of the orientation of apparatus as presented in the drawings. However, such descriptors are not intended to be in any way limiting to an intended use of the described or claimed invention.

Pressure sensors according to the present disclosure can be based on an elongate beam that is supported at one or both longitudinal ends by a rigid structure, but which is unsupported where the beam extends into a deflection zone. The deflection zone can be a medial zone between the two rigidly supported longitudinal ends of the beam or, in the case of a cantilever arrangement, the deflection zone can be in an unsupported part of the beam and preferably at an end of the beam proximal to the supported end where strain is maximised. Pressure sensors based on a beam arrangement are particularly attractive as they can be used to fabricate narrow sensors that are dimensionally suited for implantation by catheter or other delivery device into the human or animal body, and can have high sensitivity to pressure. Packaging a beam sensor with long-term hermeticity that is suitable for permanent implantation in the human or animal body, for example, is challenging.

An ideal size for ICP monitoring may be a sensor with of a width less than 2 mm. Many shunt tubes that are inserted into the brain have a diameter of 2 mm, although a larger 2.5 mm diameter tube may also be used. A similar cross section is appropriate for insertion into brain tissue. A normal ICP pressure is around 7-15 mmHg and ideally a resolution of 1 mmHg is desired for diagnosis. Pressure sensors as described above have a deformable/displaceable membrane that seals a cavity at a reference pressure and this ability of the membrane to deform/displace is reduced as the sensor width (or generally the membrane area) gets smaller. One solution to this is to make the membrane thinner and thinner, but there are practical limits to this. Another solution is to provide a flexible corrugation feature as discussed above in connection with FIGS. 1 to 3, but this may still provide limitations on how small the sensor can be made while achieving a desired pressure sensitivity.

FIG. 4 shows first and second elongate sensor devices 40, 41 each having a respective surface acoustic wave (SAW) resonator 42, 43. The first sensor device 40 may be provided on a thin piezoelectric substrate 44, e.g. crystalline quartz or aluminium nitride. This first sensor device 40 may be configured to function as a pressure sensitive resonator and the substrate 44 may have a thickness of approximately 50 microns so that it may readily deflect under pressure-induced forces. The second sensor device 41 is configured to function as a reference sensor and as such may be provided on a relatively thick substrate 45, such that there is negligible deflection or bending under the pressure-induced forces expected during normal operation.

Each sensor device 40, 41 may have at least two input/output terminals 30, 31 connected via electrical tracks 32, 33 to terminals/pads 46-49 at the ends of the substrates 44, 45 as shown. The electrical tracks 32, 33 and the pads 46-49 may be formed by metal deposition (e.g. of gold or gold-plated other metal) and suitable patterning process.

As seen in FIG. 5, the two substrates 44, 45 are bonded together in a face-to-face configuration via metal (e.g. gold) spacers 50, 51, so that the resonators 42, 43 are facing each other but spaced apart to define gap 54 or cavity therebetween. In this configuration, the two resonators 42, 43 can readily be electrically connected in parallel and can be excited through the two electrically conductive spacers 50, 51. The spacers 50, 51 may be extended longitudinally to enable external connections, as will be described further below.

As seen in FIGS. 4 and 5, the first sensor device 40 exemplifies an elongate first sensor device having a beam configuration which is supported at each longitudinal end 52, 53 by a rigid support structure which is exemplified by the thick substrate 45 and the spacers 50, 51. The gap 54 between the lower face 55 of the first sensor device 40/substrate 44 and the upper face 56 of the second sensor device 41/substrate 45 forms part of a chamber 58 into which the substrate 44 of the first sensor device 41 may deflect when pressure is applied to an upper face 57 of the substrate 44. The lower face 55 may be considered generally as an inwardly- or internally-facing face of the first sensor device and the upper face 56 may be considered generally as an inwardly- or internally-facing face of the second sensor device.

The chamber 58 and the first sensor device 40 must be hermetically sealed from the external ambient of which the pressure is to be measured, while allowing the external pressure to exert a deflecting force on the beam defined by the substrate 44 extending between the spacer supports 50, 51.

Figure 6:
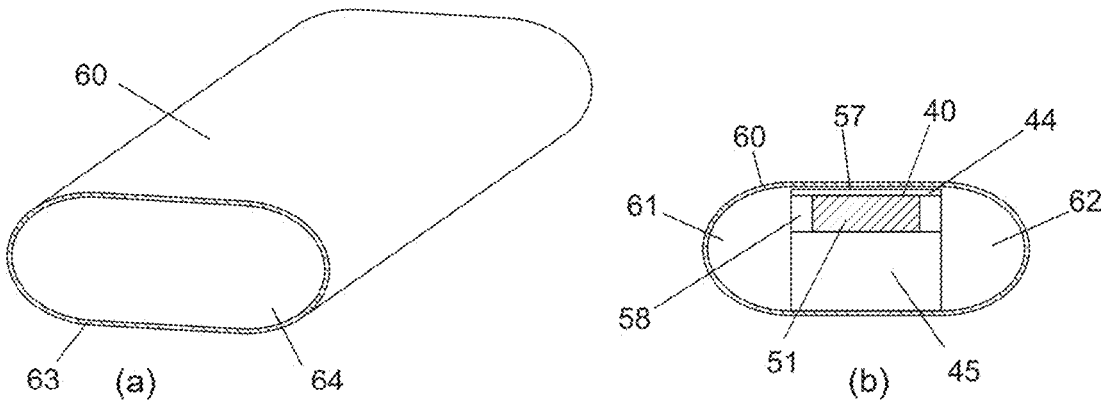
FIG. 6a is a schematic perspective view of an enclosure for the pressure sensing apparatus of FIG. 5
FIG. 6b is a schematic end view of the enclosure of FIG. 6a in position around the pressure sensing devices of FIG. 5.

With reference to FIG. 6a, hermetic packaging of the structure of FIG. 5 can be effected using a pre-formed shell, e.g. in the form of a tube 60, of suitable wall thickness, having ends 63. The wall thickness in an ICP pressure sensing apparatus may for example be 10-20 μm. The shell or tube 60 can be made from a suitable material, such as metal (including metal alloys), metallised polymer or glass, and houses the resonators 42, 43. The cross-section of the shell 60 is important as it is required to transfer pressure of the external ambient onto the beam-configured substrate 44 efficiently. An end cross-sectional view is shown in FIG. 6b. The curvature of the shell 60 may be configured to minimise the shell resistance to deformation. The shell 60 exemplifies a flexible membrane that is disposed over and coupled to the upper face 57 of the first sensor device 40. Unlike the prior art examples illustrated in FIGS. 1 to 3, the flexible membrane provided by the shell 60 extends around the sides 61, 62 of the first sensor device 40 and the chamber 58 over at least a substantial proportion of their length, rather than only extending across the upper face 57 of the first sensor device 40 and onto a surrounding rigid support structure. In this context, the expression 'sides' is intended to encompass the longitudinally extending sides 61, 62 of the sensor devices and the chamber 58. The longitudinal ends 70, 71 (FIG. 7) of the sensor devices and chamber 58 may be enclosed by a different structure, to be described below.

Figure 7:
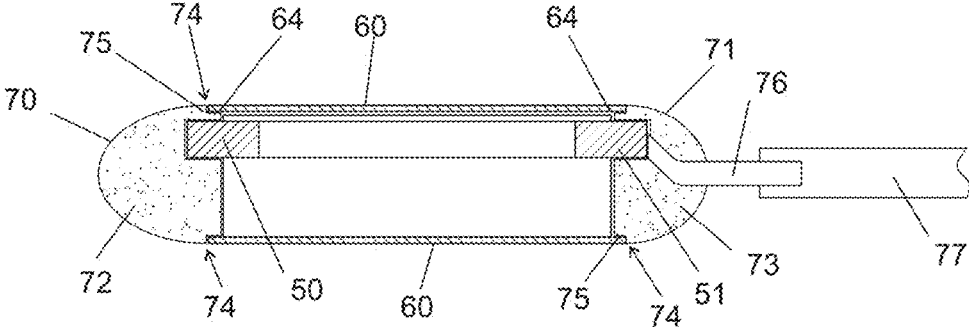
FIG. 7 is a schematic cross-sectional side view of an assembled pressure sensing apparatus.

As best seen in FIG. 7, the ends 70, 71 of the apparatus may be closed by a pair of end caps 72, 73 which engage with longitudinally-extending portions of the respective spacers 50, 51 and hermetic seals 74 are formed between the interfaces 75 of the end caps 72, 73 and the inner surfaces 64 of the shell/tube 60 just inward of the ends 63, to be described in more detail later.

The pressure sensor apparatus as described above using resonators 42, 43 takes advantage of a change in resonant frequency of SAW resonators due to induced strain and stress in the substrate 44 upon deflection. The first resonator 42 on the thin substrate 44 functions as a pressure sensitive resonator to deflect under pressure-induced forces transmitted from the ambient environment via the shell 60 to compress the gas which exists within chamber 58 at some reference pressure, e.g. below ambient pressure. The second resonator 43 is on the thick substrate 45 which is sufficiently thick that negligible deflection occurs under the pressure-induced forces.

The SAW resonators as described may have a high quality factor and operate at high frequencies (e.g. in the range of 300 MHz-2.5 GHz). These resonators can be made by depositing thin film metal electrodes and acoustic wave reflectors on the piezoelectric substrates 44, 45. They can be excited by a radio frequency (RF) signal such that the resonator picks up the energy and converts it to mechanical vibrations via piezoelectric effect. Upon quenching the excitation, the resonator continues to oscillate at its pre-determined resonant frequency. If the SAW resonator substrate is deflected, the induced stress and strain in the substrate causes a shift in the resonant frequency. The first resonator 42 on the thin substrate 44 lies over the gas-filled or vacuum cavity in chamber 58 which defines the reference pressure. Any change in the environmental (ambient) pressure outside the shell 60 creates a differential pressure with respect to the cavity pressure and induces strain/stress in the membrane 60, causing a shift in the resonant frequency that is proportional to the pressure. The second resonator 43 on the thick substrate 45 will not be affected by the pressure change and will not change in resonant frequency as a result of the ambient pressure changes. It can therefore be used as a reference.

The resonators 42, 43 can be coupled to an antenna and be excited wirelessly by sending a RF pulse at a frequency close to resonance. Part of the RF pulse energy is stored in the resonator and is radiated back as a weak decaying RF wave, once the transmitting pulse is switched off. This signal is detected by a receiver and its frequency is estimated to obtain pressure. An RF transceiver can be used to interrogate the sensor. In transmit mode, the interrogator may send RF bursts of, e.g., ~2 µs duration to excite a resonator. At the end of each pulse, the interrogator is switched to its receiving mode to detect the decaying signal. An on-board processor calculates the frequency and converts it to pressure.

Thus, where resonators 42, 43 are used for the sensor devices, provision is made for such an RF interface. With further reference to FIG. 7, one end cap, e.g. end cap 72 may be used to provide a ground plane. The shell 60 is formed from an electrically conductive material, as is the end cap 72. The two components are bonded together, e.g. by welding or soldering, such that electrical continuity is maintained. The end cap 72 is also electrically connected to the spacer 50 and thereby to the terminals 46, 48 of the first and second resonators respectively. In this way one of the input/output terminals 31 of the resonators 42, 43 is connected to a ground plane that surrounds a substantial part of the device.

The other end cap 73 may also have an electrically conductive outer surface which is electrically bonded to the shell 60, extending the ground plane to the end 71 of the device, as well as providing a hermetic seal. The end cap 73 may also have an electrically insulating outer surface which is bonded to the shell 60 by an electrically insulating material, such as glass, ceramic or glue to provide a hermetic seal. However, this end cap 73 also provides an electrical feed-through 76 which is electrically continuous with the spacer 51 and thereby to the terminals 47, 49 of the first and second resonators 42, 43 respectively. The electrical feed-through 76 is electrically isolated from the ground plane formed by the shell 60, the end cap 72 and the outer surface of the end cap 73.

The electrical feed-through 76 is couplable to an antenna 77 of a suitable type, examples of which are described below.

Figure 8:
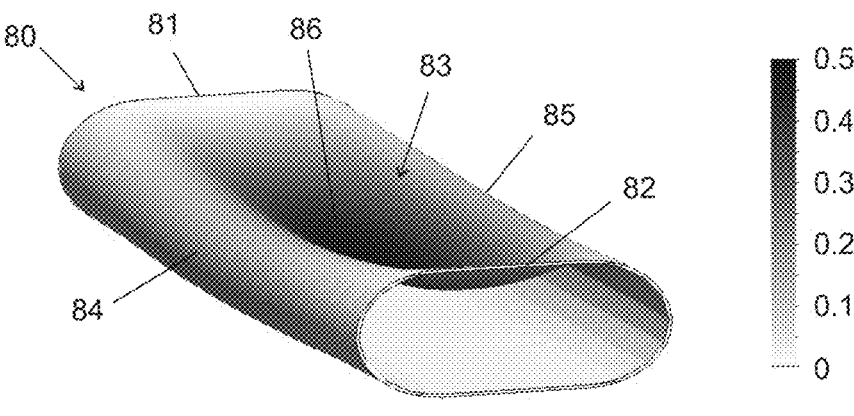
Figure 9:
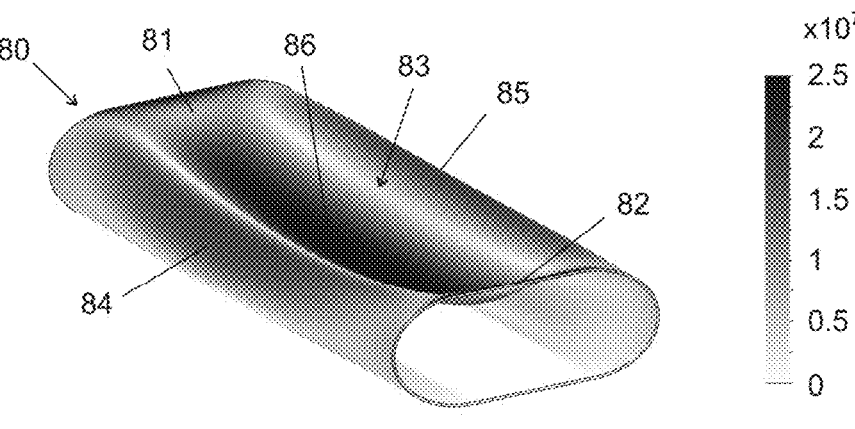
FIG. 9 is a 3D simulation showing the surface von Mises stress in the enclosure of FIG. 6a arising from the surface displacement seen in FIG. 8.

The shell 60 may generally take the form of a flexible tube or sleeve 80 having a flattened circular cross-section as illustrated in FIGS. 8 and 9. The sleeve has first and second end regions 81, 82 which, in the assembled pressure sensing apparatus, are coupled to and supported by the end caps 72, 73. The central region 83 may be generally unsupported except by its contact with the upper face 57 of the deflectable substrate 44 and by its contact with the base or underside of the rigid substrate 45. At least the upper parts of the sides 84, 85 of the central region 83 are free to flex unsupported by, and not in contact with, the support structure defined by the rigid substrate 45, the spacers 50, 51 and the end caps 72, 73. In this way, the flexible membrane exemplified by the shell 60 is free to flex not only in its top region 86 but also in the central part of its side regions 84, 85. Inward deflection of the top region 86 which would otherwise tend to be inhibited by the need for the membrane to stretch to enable the required out-of-plane movement is in this instance substantially eased by the ability of the side walls/side regions 84, 85 to also deflect inwards and/or outwards thereby reducing tension in the membrane top region 86. FIG. 8 illustrates total surface displacement and FIG. 9 illustrates surface von Mises stress indicating the spreading of the stress from the beam deflection to the side regions of the 84, 85 of the shell 60. The ability of the side walls/side regions 84, 85 of the shell to deflect inwards and/or outwards can assist the top region 86 of the shell 60 to deflect inwards by (i) a reduced or eliminated stretching requirement of the shell material because the side regions can also deflect inwards, and/or (ii) enabling the shell to reduce the curvature of the side regions 84, 85 otherwise required to accommodate inward deflection of the top region, e.g. by allowing an outward bulging of the side regions. The exact extent and relative location of inward and/or outward deflection of the various parts of the side regions will depend on the properties of the shell material, for example, elasticity and stiffness as well as the shell geometry. In a general aspect, the inward and/or outward movement of the side regions 84, 85 of the shell enables an overall reduction in stress in the shell undergoing deflection in the top region 86, thereby decreasing resistance to deflection of the top region and increasing sensitivity of the pressure sensor.

The shell forming the flexible membrane may be fabricated using any suitable method. For example, a metal shell may be extruded from, for example, nitinol or other shape memory alloy, and may have a thickness of 30 to 40 microns for example. This can be thinned, using a suitable technique such as polishing or electropolishing, to between 10 and 15 microns thickness, for example. The thinning process may be implemented selectively in target areas for optimum flexibility response.

Figure 2:
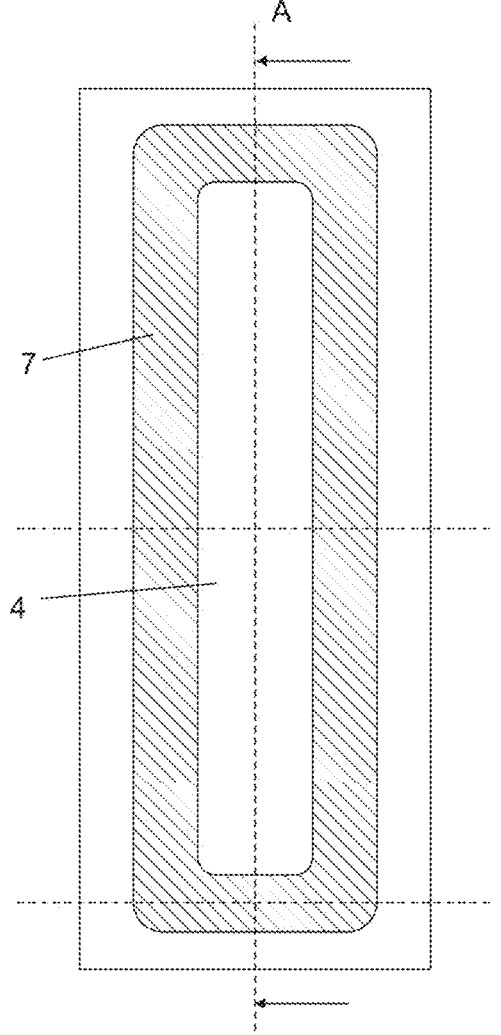
FIG. 2 is a schematic plan view of the prior art pressure sensor of FIG. 1 as discussed above.

The sensitivity of the pressure sensing device described is improved as the pressure-induced forces required to deflect the beam-configured first sensor device 40 via the membrane/shell 60 can be reduced from the prior art configurations shown in FIGS. 1 to 3. In the arrangement of FIGS. 4 to 7, the flexible membrane provided by the shell is held rigidly where it contacts the longitudinal ends at the rigid structure and the rigid base of the substrate 45, but not where the flexible membrane extends along sides of first sensor device 40 and the chamber 58, to thereby provide additional flexibility.

There are numerous ways of fabricating the shell and connecting it to the rest of the assembly.

In the example of FIG. 7, the shell 60 may be a metal or metal alloy sleeve sealed to the two end caps 72, 73 by, e.g. soldering or welding to form the hermetic seal and thereby defining an envelope which hermetically seals the first and second sensor devices 40, 41 and the chamber 58 that is disposed between them. The metallic nature of the sleeve 60 and the direct soldering or welding to the metal or metallised surfaces of the end caps provides the ground plane for the antenna.

A similar arrangement can be provided where the shell 60 is made from a suitable polymer whose outer or inner surface is metallised to provide the ground plane as well as to provide better long term hermeticity. A suitable metallisation layer may be, for example 0.2-5 microns in thickness. Completing the seal of this shell 60 to the end caps 72, 73 may be effected differently, as welding or soldering of the polymer is not possible. The shell may instead be bonded to the end caps 72, 73 by a suitable adhesive to form an at least temporary seal. The seams between the shell 60 and the two end caps 72, 73 may be covered by electroplating or vapour deposition to ensure long term hermeticity and electrical continuity. The adhesive may be selected to resist electrolyte ingress during the electroplating process.

Figure 13:
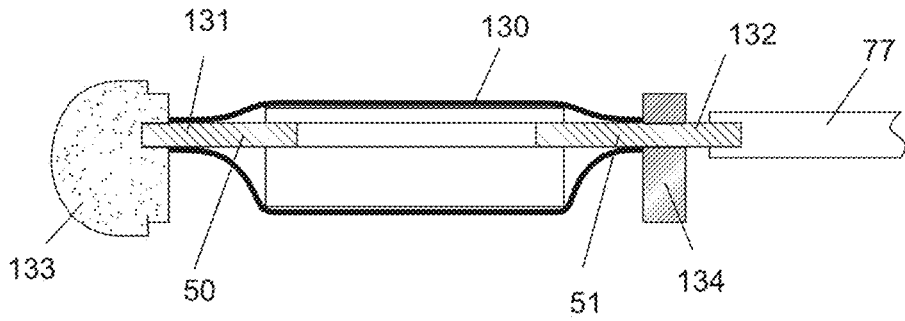
FIG. 13 is a cross-sectional side view of a pressure sensing apparatus with a hermetically sealed glass envelope.

In another arrangement, the shell 60 may comprise a thin-walled glass tube to provide the hermetic seal while being thin enough to be flexible to provide for deflection under pressure. The assembly of FIG. 5 may, for example, be inserted into a glass tube of suitable cross section, so that the metal spacers 50, 51 are respectively protruding from each end. The hermetic seal can be completed by heating the glass tube at each end. This may soften/melt the glass tube sufficiently to seal around the metal spacers 50, 51 to form a capsule while leaving a portion of each spacer extending longitudinally out of the capsule, as shown in FIG. 13. The portions 131, 132 of the two metal spacers extending out of the hermetically sealed capsule 130 form the electrical contacts. As seen in FIG. 13, this arrangement may also include a metal cap 133 coupled to the contact portion 131 and a ceramic cap 134 coupled to the contact portion 132.

Also as seen in FIG. 13, one of these contacts 132 can be electrically connected to an antenna 77 similar to the arrangement of FIG. 7. The other contact 131 can be coupled to a ground plane extending around the capsule by the metal cap 72 or 133. The ground plane may also be formed by metallising the outer surface of capsule 130.

Figure 14:
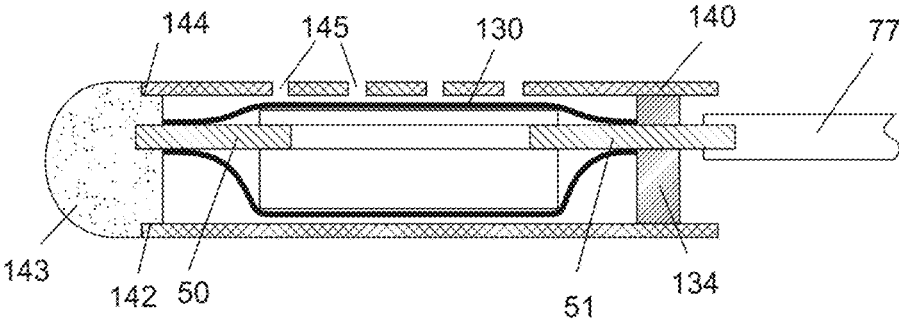
FIG. 14 is a cross-sectional side view of a pressure sensing apparatus with a ground-plane sleeve surrounding the sealed envelope.

The ground plane can generally be formed as a sleeve around the capsule. In the example of FIG. 14, a sleeve 140 may be a rigid metal tube into which the capsule, e.g. capsule 130 or shell 60, is inserted and the ground plane contact 142 of the end cap 143 can be welded, soldered or otherwise connected thereto. The sleeve 140 may be formed of the same material as the spacers 50, 51. Using the same electrically conductive materials for parts of the apparatus that are exposed to, for example, ionic liquids in the body— such as live tissues—may be particularly advantageous to avoid chemical reactions where two dissimilar metallic materials are electrically connected together. If two dissimilar metals are electrically connected and placed into such an ionic medium, a short circuit battery may be formed resulting in chemical reactions as well as corrosion of the parts.

The distal end 144 of the metal tube 140 that is coupled to the ground plane contact 142 (e.g. the non-antenna end) or the distal end of the end cap 143 (or both) may be configured with a suitable profile such as rounded or tapered as seen in FIG. 14 to prevent tissue damage during implantation, where it may form the distal end of the pressure sensing apparatus as it is introduced into the body by a suitable catheter/guidewire arrangement. Part of the metal sleeve 140 may be removed or may contain holes 145 or other apertures to allow transmission of ambient pressure to the capsule surface.

The glass capsule body may be further encapsulated in a thin polymer layer, e.g. silicone or Parylene C for protection.

Figures 10, 11:
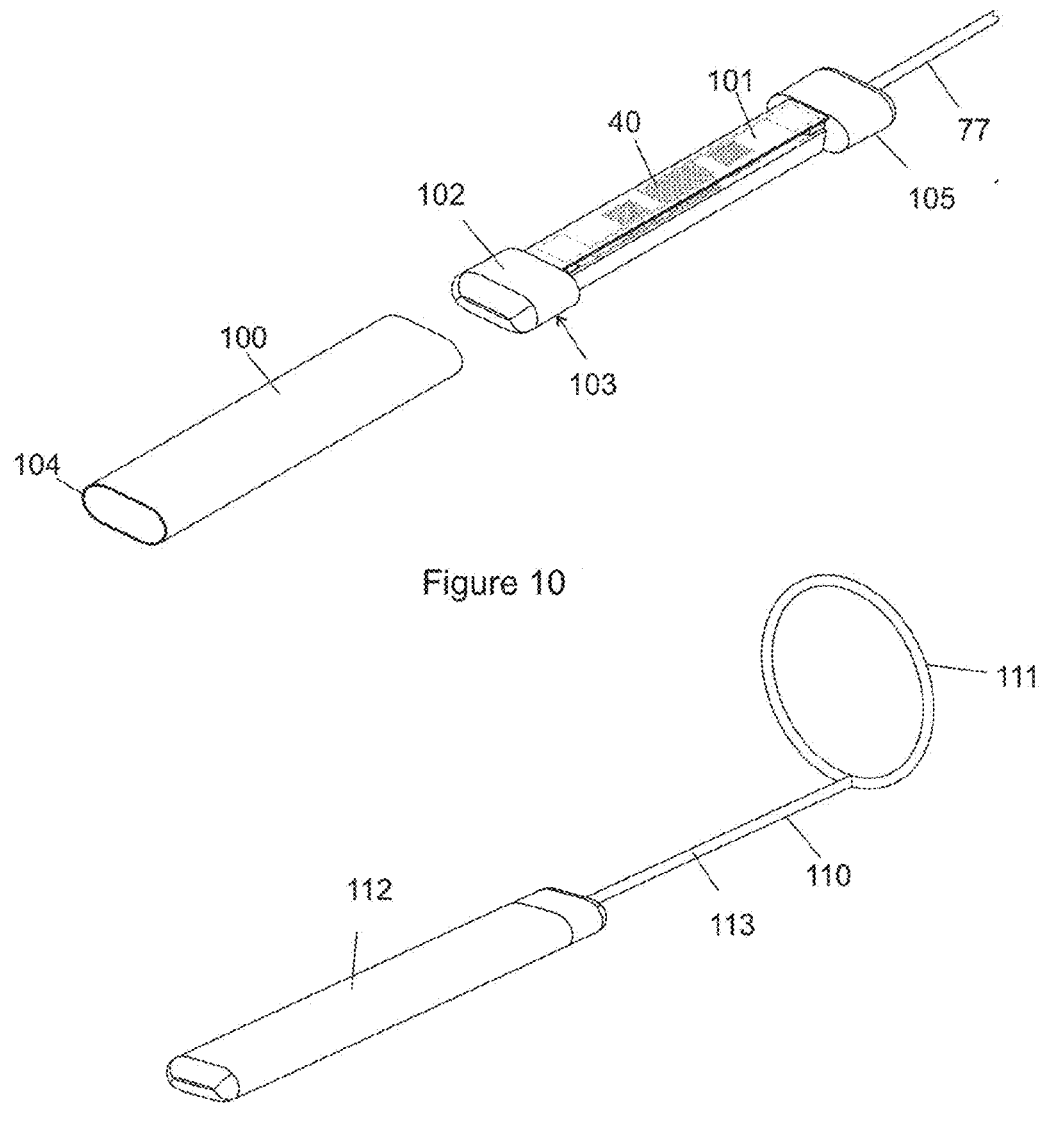
FIG. 10 is a schematic perspective view of a partly assembled pressure sensing apparatus.
FIG. 11 is a schematic perspective view of the assembled pressure sensing apparatus of FIG. 10.

FIG. 10 shows a schematic perspective view of a partially assembled pressure sensing apparatus similar to that shown in cross-sectional view in FIG. 7. The tube forming the shell 100 may be slid on to or otherwise applied to the body 101 incorporating the sensor device 40. End cap 103 is soldered or otherwise electrically connected to the distal end 104 of the shell 100, as described above, to form the ground plane 102. An antenna 77 is connected via the end cap 105.

Although the spacers 50, 51 described above have been described as being formed of metal to provide a convenient electrical connection to each of the terminals/pads 46-49, it will be understood that non-conducting rigid material such as ceramic could be used and separate provision for electrical connection to the first and/or second sensor devices 40, 41 made using conductive coatings or conducting tracks/vias extending along or through the spacers. Such an arrangement may be useful, for example where the first sensor device is formed as a cantilever beam structure such that both the first and second input/output terminals 30, 31 and their respective tracks 32, 33 must be connected to a ground plane and antenna via one end of the apparatus since the other end of the beam is unsupported.

Suitable antenna connection arrangements can be particularly important when using the pressure sensing apparatus for intracranial implants.

Figure 12:
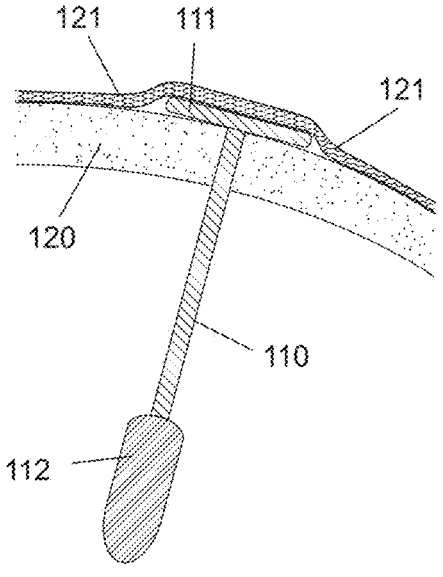
FIG. 12 is a schematic cross-sectional view of a patient's cranium with a pressure sensing apparatus installed.

An antenna such as antenna 77 of FIG. 7 can be made from gold plated or cladded nitinol wire which can also be used mechanically to insert the implant. As seen in FIGS. 11 and 12, an antenna 110 extends from a pressure sensing apparatus 112 such as described above, and the end of the antenna 110 may be terminated with a continuous or discontinuous loop 111 or other laterally-extending portion. The loop may be configured with a suitable diameter such that it can remain on the skull 120 subcutaneously, i.e. beneath the cutaneous layer 121. Preferably, the antenna material is chosen to have superelastic shape memory properties such that the loop 111 can be elongated and placed in a pusher tube for implantation. Once the implant is inserted, the loop 111 then re-expands to its pre-formed shape and sits on the skull 120, positioning the implant at the desired depth. The skin 121 can be closed over the antenna 110, 111 thereby substantially reducing risks of infection, and the pressure sensing apparatus can be activated and interrogated by a suitable transceiver (e.g. mounted within a cap worn by the patient) in communication with the wireless RF interface provided by the antenna 110.

The arrangement of FIGS. 10 and 11 exemplifies an antenna comprising a resilient material having an expanded shape memory configuration which defines a substantially linear axial portion such as shaft 113 and an off-axis, laterally-extending portion such as loop 111. The material at least of the loop 111 is resiliently bendable into a substantially linear configuration for delivery of the apparatus via a catheter. Other possible forms of antenna are possible. For example, with reference to FIG. 15, the antenna 150 may comprise a radially extending portion 151 coupled to the shaft 113 and extending laterally away from the shaft axis, which supports a continuous or discontinuous loop 152 around the shaft or device axis as exemplified in FIG. 15a. The antenna 153 may comprise a discontinuous loop 154 coupled directly to the antenna shaft 113 as exemplified in FIG. 15b. The antenna 155 may comprise a spiral element 156 coupled directly to the antenna shaft 113 as exemplified in FIG. 15c. The spiral element 156 may be used for antenna tuning. The antenna 157 may comprise a loop 158 coupled directly to the antenna shaft 113 and the antenna shaft may include a coil 159 forming part of the shaft 113, e.g. for antenna tuning, as exemplified in FIG. 15d. In a general aspect, each of the antenna designs described above may be considered to exemplify an antenna with an axially extending portion (e.g. shaft 113) and an off-axis laterally extending portion such as the portion 151 or the loop portions that extend away from or around the axially extending portion as found in portions 154, 156, 158. It will be understood that various features of the antennae of FIGS. 11, 12 and 15 may be combined in different ways.

Figure 16:
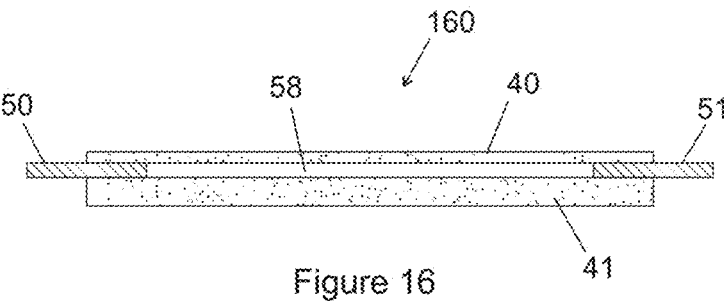
FIG. 16 is a simplified schematic cross-sectional side view of the pressure sensing apparatus of FIG. 5.

In another arrangement, the rigid support structure may comprise a housing having a trench within which the first sensor device is positioned. FIG. 16 is a simplified cross-sectional side view of the pressure sensing apparatus 160 described with reference to FIG. 5 in which first 40 and second 41 sensor devices are spaced apart from one another in a face-to-face configuration via metal spacers 50, 51 to define a chamber 58 therebetween. The metal spacers 50, 51 are electrically connected to the SAW resonators of the first 40 and second 41 sensor devices to enable the formation of external connections. In this respect, the metal spacers 50, 51 may be referred to as "electrical terminals" in this example.

Figure 17:
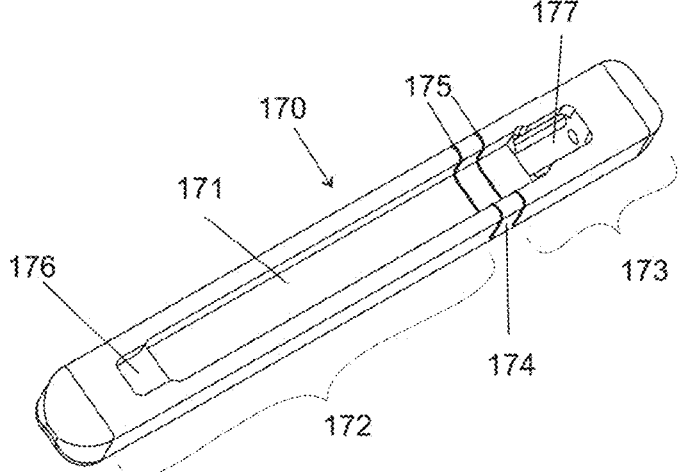
FIG. 17 is a schematic perspective view of a housing to support the pressure sensing apparatus of FIG. 16.

FIG. 17 shows one example of a housing 170 suitable for use with the pressure sensing apparatus 160 of FIG. 16. The housing 170 may be made from a suitable insulating material such as sapphire, biocompatible ceramic (e.g. zirconia) or a hard biocompatible polymer, and may comprise first 172 and second 173 electrically conductive portions separated from one another by an electrically insulating portion 174. This can be achieved by coating the surface of the housing 170 with a conductive layer of metal (e.g. gold) and subsequently removing the conductive coating in the area 174 shown between the two dark lines 175. Alternatively, if the housing 170 is formed from a ceramic, selected portions 172, 173 of the housing 170 may be made conductive by selectively adding a conductive material to these portions 172, 173 before sintering the ceramic.

In the example shown in FIG. 17, the first electrically conductive portion 172 is substantially longer than the second electrically conductive portion 173 to form a ground plane. Furthermore, the trench 171 of the housing 170 is narrower at the ends 176, 177 to support the metal spacers 50, 51 and is wider therebetween to enable unrestricted displacement of the deflectable portion at one or two sides of the first sensor device 40 (ideally with a clearance of 50-100 μm between the sides of the first sensor device 40 and the sides of the trench 171).

Figure 18:
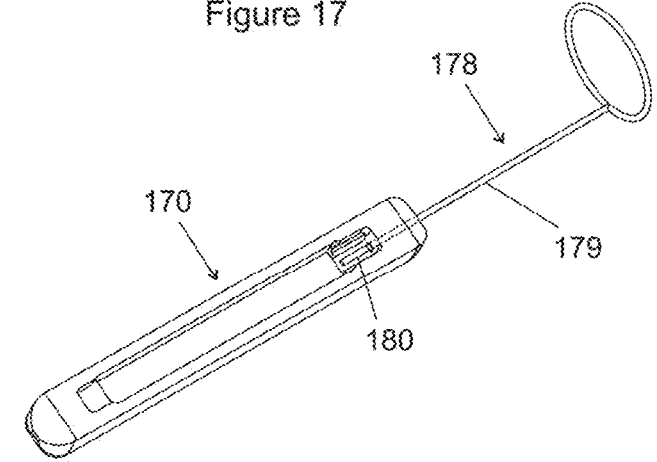
FIG. 18 is a schematic perspective view of the housing of FIG. 17 electrically coupled to an antenna.

FIG. 18 shows the housing 170 of FIG. 17 electrically coupled to an antenna 178. In this example, the antenna pole 179 is inserted and integrated into the housing 170 such that the antenna pole end 180 is electrically exposed. This allows electrical connection of the antenna pole 179 to the second (shorter) electrically conductive portion 173. In this way, one of the metal spacers 50 (and hence one terminal of the SAW resonators that are connected in parallel) can be electrically connected to the ground plane and the other 51 can be electrically connected to the antenna pole 179. The combination of the antenna pole 179 and the ground plane forms an electromagnetic radiating structure and enables the SAW resonators to receive and transmit electromagnetic waves.

FIGS. 19a and 19b show assembly of the pressure sensing apparatus 160 of FIG. 16 with the housing 170 of FIG. 18. Once the pressure sensing apparatus 160 has been positioned within the trench 171 of the housing 170, the first 172 and second 173 electrically conductive portions may be conductively bonded to a respective metal spacer 50, 51 to connect the SAW resonators to the ground plane and antenna 178.

As mentioned previously, the chamber 58 formed between the first 40 and second 41 sensor devices must also be hermetically sealed from the external environment whilst allowing the external pressure to exert a deflecting force on the beam of the first sensor device 40. This can be achieved by encapsulating (substantially or completely) the assembled structure 181 of FIG. 19b in a flexible polymer membrane to form the envelope.

FIG. 20 shows a cross-sectional end view of the assembled structure 181 of FIG. 19b after encapsulation.

The flexible polymer membrane 182 is preferably made from an elastomer (e.g. silicone or polyurethane), but other polymers may be used instead. As illustrated in FIG. 20, the flexible polymer membrane 182 extends around all sides of the assembled structure 181 (and thus the pressure sensing apparatus 160). In this way, deformation of the flexible polymer membrane 182 (by indentation on top 183 and stretching or reconfiguration elsewhere) allows for ease of deflection of the beam of the first sensor device 40 under pressure.

The envelope may be preformed as a casing into which the assembled structure 181 is inserted before being sealed. Alternatively, the envelope may be formed on the assembled structure 181 using polymer coating techniques to deposit the flexible polymer membrane 182. For example, the assembled structure 181 may be dip-coated in a polymer solution. In this scenario, the ingress of polymer into the trench 171 of the housing 170 should be prevented otherwise the polymer may restrict the beam deflection and dampen the sensed signal. Prevention is possible by adjusting the viscosity of the polymer solution with respect to the clearance between the sides of the first sensor device 40 and the sides of the trench 171. The larger the clearance and lower the viscosity, the easier it is for the solution to enter the trench 171. In practice, the clearance should be as narrow as possible whilst allowing for the full range of displacement.

The flexible polymer membrane 182 may be deposited only around the housing 170 leaving a substantial part of the antenna 178 uncovered, or it may encapsulate the whole structure 181 including the antenna 178. Furthermore, once the flexible polymer membrane 182 has been deposited, the hermeticity of the resulting envelope may be increased by depositing one or more additional layers of material on top of the flexible polymer membrane 182 to cover any pores in the polymer. This can be achieved using thin film coating techniques (e.g. using ALD or PVD) to deposit an additional layer of polymer (e.g. Perylene C), metal (e.g. gold), inorganic material (e.g. an oxide or nitride) or a combination of these.

Providing a sensor of adequate pressure sensitivity and small width is challenging, particularly when such a deeply implanted sensor should be readable wirelessly. This is not least due to the fact that the signal received from the implant is often weak and embedded in noise. The design described above may resolve to 1 mmHg pressure changes using the described SAW-based pressure sensor with a SAW resonator formed on a quartz substrate. The wireless operation and the small size enable it to be fitted into the tip of a catheter and to wirelessly communicate with an external device. Since there need be no cable penetration through the scalp 121, the complications of infection, breakage and dislodgement can be eliminated or substantially reduced, resulting in improved patient mobility and the opportunity for continuous ICP measurement in a ventricle or the brain tissue. The pressure sensing apparatus can be implanted as a standalone unit, if required.

The pressure sensing apparatus as described can turn a shunt from a passive device to a smart device with a pressure measurement function, which provides a baseline for adjusting a valve and detecting blockage. The measured pressure may also be used as feedback for active valve control. The device may benefit normal pressure hydrocephalus (NPH) patients. The current methods of NPH diagnosis are based on symptoms as well as MRI and CT scans. Although the "gold standard" of diagnosing NPH is an improvement of symptoms with ventricular shunting, an ICP monitoring device with or without drainage capability is likely to improve the NPH diagnosis and identify the candidates for permanent shunts. If a ventriculoperitoneal (VP) shunt is required, a conventional shunt can be connected to the pressure sensing apparatus as described herein. The device can be removed with minimal operation.

The pressure sensing device can offer a high quality factor and high operating frequency for battery-less SAW based sensors, allowing continuous monitoring using a light weight low power electronic reader. Other resonant sensors (such as MEMS based) may typically work at much lower frequencies (e.g. at least an order of magnitude lower) and have low quality factors (e.g. two orders of magnitude lower). This means that relevant electronic readers cannot operate in radiation mode but rather work by inductive coupling. Sensor interrogation with this technology requires higher power and, as a consequence, the readers are bulkier and less suitable for use as a wearable technology.

The specific packaging methods for the pressure sensor allow for using a resonator as a beam structure. This means that the sensor width (compared to other resonator sensor packaging technologies) can be significantly smaller, while maintaining a high pressure sensitivity. This is particularly important for integration of the sensor with an intracranial shunt or direct implantation in the brain.

The combination of the above-mentioned features also allows for a low profile sensor antenna that does not require a bulky pick up loop, which would otherwise be required for inductively coupled systems. This is particularly advantageous for integration of the pressure sensing apparatus with shunts, as the antenna can be a very thin and short wire positioned inside a shunt tube in a manner that does not compromise the patency of the shunt tube. In case of a standalone implant, the antenna can be dimensioned for the desired sensor depth in brain tissue and can be easily fixed subcutaneously as described above.

The whole pressure sensing apparatus can be constructed with a form factor suitable for placement at the end of a shunt tube that may be implanted into the brain. A short flexible tube may be inserted into the brain with the wireless and battery-less pressure sensing device therein. The short tube is connected to a long tube that extends subcutaneously into the abdomen where the CSF can be discharged and absorbed. Such a shunt could include a valve arrangement to enable control of the flow of CSF from brain to abdomen. The pressure sensing apparatus as described herein may be configured to control the valve to maintain an appropriate intracranial pressure, e.g. in a closed loop feedback configuration, or the valve may operate under control of the pressure sensing apparatus when initiated from an externally applied signal.

Various modifications and adaptations of the pressure sensing apparatus as described above are possible.

Although the flexible membrane provided by the shell 60 has been illustrated as extending around the entire periphery of the first and second substrates 44, 45 of the first and second sensor devices 40, 41 and the gap 54 between them, it will be understood that the shell defining the flexible membrane could extend around the sides of the first substrate and the gap 54 between the substrates, and be secured to the rigid substrate 45 along its sides. Although optimum performance of the flexible membrane provided by the shell can be provided by having the membrane free to flex inwardly and/or outwardly on both sides of the device in at least the central region as discussed above, it will be understood that having the freedom of movement on only one side may also be advantageous.

Other ways of improving hermeticity of a polymer shell 60 may include incorporation of oxide or nitride layers (e.g by Atomic Layer Deposition process) on the polymer layer. Mutilayers of polymer, metal, oxide or nitride may also be advantageous.

It will be understood that deploying the beam sensor in a cantilever configuration may require that the tracks 32, 33 connecting to the inputs/outputs 30, 31 of the sensors be connected to the same, cantilevered end of the rigid structure with suitable arrangements for antenna and ground plane connections.

Although the examples of a pressure sensing apparatus given above have used an acoustic wave device whose resonant frequency may change as a result of flexing of the device substrate under pressure changes, it will be recognised that other forms of sensing device may be used that can provide a transducer output as a function of flexing/displacement of the substrate on which they are formed. For example, a capacitive sensor or piezo-resistive sensors could be used.

The pressure sensing devices as described herein can readily be formed into capsules of length 10 mm or less, and width/diameter of 2-3 mm or less.

Although examples have been described in the context of use for intracranial pressure monitoring applications, the pressure sensing apparatus arrangements as described herein can be readily used, modified and/or adapted for use in other applications.

Other embodiments are intentionally within the scope of the accompanying claims.

The invention claimed is:

1. A pressure sensing apparatus comprising:
an elongate first sensor device in a beam configuration supported at at least one longitudinal end by a rigid support structure and having a deflectable portion;
a chamber disposed adjacent a first face of the first sensor device;
an envelope hermetically sealing the first sensor device and the chamber from an ambient environment;
the envelope comprising a flexible membrane disposed over and coupled to a second face of the first sensor device and extending along at least one or two sides of the first sensor device and the chamber, in which the rigid support structure comprises a housing having a trench within which the first sensor device is positioned, and the flexible membrane comprises a polymer which encapsulates the housing to form the envelope, in which the housing comprises first and second electrically conductive portions separated from one another by an electrically insulating portion, each electrically conductive portion coupled to a respective electrical terminal of the first sensor device, and in which the first electrically conductive portion of the housing is substantially longer than the second electrically conductive portion to form a ground plane, and the second electrically conductive portion of the housing is coupled to an antenna.

2. The pressure sensing apparatus of claim 1 configured such that pressure applied to the flexible membrane at the second face causes deflection of the flexible membrane disposed over the deflectable portion of the first sensor device and displacement of the flexible membrane along said at least one or two sides of the first sensor device and the chamber.

3. The pressure sensing apparatus of claim 1 in which the flexible membrane of the envelope surrounds the first sensor device, the chamber and the support structure along at least a portion of a longitudinal axis of the first sensor device.

4. The pressure sensing apparatus of claim 3 in which the flexible membrane forms a sleeve extending along the longitudinal axis and around the first sensor device, the chamber and at least a portion of the support structure.

5. The pressure sensing apparatus of claim 4 in which the support structure comprises two longitudinal end portions which each close a respective end of the sleeve to form the hermetic seal of the envelope.

6. The pressure sensing apparatus of claim 5 in which the longitudinal end portions each comprise an electrically conductive cap which is bonded to the respective end of the sleeve around its circumference to form the hermetic seal.

7. The pressure sensing apparatus of claim 1 in which the elongate first sensor device is supported at each longitudinal end by the rigid support structure and the deflectable portion is a deflectable central portion between the opposing longitudinal ends.

8. The pressure sensing apparatus of claim 7 in which a base of the rigid support structure comprises a second sensor device extending parallel to the first sensor device adjacent the chamber.

9. The pressure sensing apparatus of claim 8 in which the rigid support structure further comprises a pair of spacers separating the base and first sensor to form the chamber, the spacers each comprising an electrically conductive material coupled to a respective electrical terminal of at least one of the first sensor device and the second sensor device.

10. The pressure sensing apparatus of claim 9 in which the envelope comprises an electrically conductive material electrically coupled to a first one of the spacers and forming a ground plane enveloping at least a part of the first sensor device.

11. The pressure sensing apparatus of claim 9 in which the electrically conductive material of a second one of the spacers is electrically connected to an antenna extending away from the envelope.

12. The pressure sensing apparatus of claim 11 in which the antenna comprises a resilient material having an expanded shape memory configuration defining a substantially linear axial portion and an off-axis laterally extending portion, the material resiliently bendable into a substantially linear configuration for delivery of the apparatus via a catheter.

13. The pressure sensing apparatus of claim 1 in which the flexible membrane comprises a metal material soldered, welded or otherwise bonded directly to at least one electrically conductive end cap of the envelope.

14. The pressure sensing apparatus of claim 1 in which the flexible membrane comprises a metallised polymer bonded to at least one electrically conductive end cap of the envelope and electrically continuous therewith by an electroplated layer.

15. The pressure sensing apparatus of claim 1 in which the flexible membrane comprises a glass material forming the envelope as a closed-ended capsule sealed around at least one electrical connection passing therethrough.

16. The pressure sensing apparatus of claim 15 in which the closed-ended capsule is sealed around at least two electrical connections passing therethrough, and further including an electrically conductive sleeve disposed around the capsule electrically connected to one of the electrical connections to form a ground plane around the capsule.

17. The pressure sensing apparatus of claim 1 in which ends of the trench of the housing are narrower to support the respective electrical terminals of the first sensor device and wider therebetween to enable unrestricted displacement of the deflectable portion.

18. The pressure sensing apparatus of claim 1 in which the flexible membrane is coated with one or more layers of material to increase the hermeticity of the envelope.

19. The pressure sensing apparatus of claim 1 incorporated within an intracranial shunt apparatus.

20. The pressure sensing apparatus of claim 19 further including a valve within the intracranial shunt apparatus, the valve being configured for control by an output of at least the elongate first sensor device.

* * * * *